United States Patent [19]

Caruthers et al.

[11] 4,415,732

[45] Nov. 15, 1983

[54] PHOSPHORAMIDITE COMPOUNDS AND PROCESSES

[75] Inventors: Marvin H. Caruthers; Serge L. Beaucage, both of Boulder, Colo.

[73] Assignee: University Patents, Inc., Norwalk, Conn.

[21] Appl. No.: 248,450

[22] Filed: Mar. 27, 1981

[51] Int. Cl.$^3$ ............................................. C07H 17/00
[52] U.S. Cl. ....................................... 536/27; 536/28; 536/29
[58] Field of Search ............................ 536/27, 28, 29

[56] References Cited

U.S. PATENT DOCUMENTS 3,534,017 10/1970 Fujimoto et al. ..................... 536/29

FOREIGN PATENT DOCUMENTS 35719 9/1981 European Pat. Off. .
61746 10/1982 European Pat. Off. .

OTHER PUBLICATIONS

Chem. Abstracts 79:146775j.
Adams et al., J. Am. Chem. Soc. '83, vol. 105, No. 3, pp. 661–663.
Matteuci et al., J. Am. Chem. Soc. 103(11), pp. 3185–3191(1981).
Beaucage et al., Tetrahedron Letters, 22(20), pp. 1859–1862(Apr. 28, 1981).

*Primary Examiner*—Ethel G. Love
*Attorney, Agent, or Firm*—Scully, Scott, Murphy & Presser

[57] ABSTRACT

A new class of nucleoside phosphoramidites which are relatively stable to permit isolation thereof and storage at room temperature. The phosphoramidites are derivatives of saturated secondary amines.

20 Claims, No Drawings

PHOSPHORAMIDITE COMPOUNDS AND PROCESSES

The inventions described herein were made in the course of work under a grant or award from the Department of Health, Education and Welfare.

This invention relates to new and useful Phosphorus compounds which are particularly useful in the production of oligonucleotides.

CROSS REFERENCE

M. H. Caruthers et al. copending and commonly assigned patent application Ser. No. 247,144 filed Mar. 24, 1981.

BACKGROUND OF THE INVENTION

1. Field of the Invention

The present invention relates to new and useful phosphoramidites which are intermediates for polynucleotides synthesis, as well as the improved process for production of oligonucleotides from which polynucleotides are prepared.

2. Description of the Prior Art

Numerous attempts have been made to develop a successful methodology for synthesizing sequence defined oligonucleotides. However, the stepwise synthesis of polynucleotides, and specifically oligonucleotides still remains a difficult and time consuming task, often with low yields. One prior art technique has included the use of organic polymers as supports during polynucleotide synthesis. Classically the major problems with polymer supported synthesis strategies has been inherent in the nature of the polymer support. Various prior art polymers used in such synthesis have proven inadequate for reasons such as: (1) slow diffusion rates of activated nucleotides into the support; (2) excessive swelling of various macroporous, low cross-linked support polymers; and (3) irreversible absorption of reagent onto the polymer. See for example, V. Amarnath and A. D. Broom, *Chemical Reviews* 77, 183-217 (1977).

Modified inorganic polymers are known in the prior art, primarily for use as absorption materials, for example, in liquid chromatography. The attachment of nucleosidephosphates to silica gel using a trityl linking group is described in the prior art (H. Koster, *Tetrahedron Letters*, 1527-1530, 1972) but the method is apparently applicable only to pyrimidine nucleosides. The cleavage of the nucleoside from the silica support can only be accomplished with acid to which the purine nucleosides are sensitive.

The production of phosphotriester derivatives of oligothymidylates is described in literature (R. L. Letsinger and W. B. Lunsford, *Journal of the American Chemical Society*, 98:12, 3655-3661) by reaction of a phosphorodichloridite with a 5'-O blocked thymidine and subsequent reaction of the product with a 3'-O blocked thymidine followed by oxidation of the resulting phosphite to a phosphate and removal of blocking groups to obtain the phosphotriesters; using this procedure, the tetramer and pentamer products, dTpTpTpT and TpTpTpTpT in which T is thymidine were prepared. Unfortunately, the process requires separation and purification of products at each stage to ensure proper sequencing of the added nucleosides. Separation techniques including precipitation and washing of precipitates are necessary to implement each successive stage reaction.

In the aforementioned commonly assigned patent application are described methods for forming internucleotide bonds, i.e. bonds linking nucleosides in an oligonucleotide or polynucleotide, by reaction of halophosphoridites with suitably blocked nucleoside or oligonucleotide molecules.

The deoxynucleoside-modified silica gel is condensed with a selected nucleoside through formation of a triester phosphite linkage between the 5'-OH of the deoxynucleoside. The phosphite linkage can be produced by first incorporating the phosphite group onto the 5'-OH of the nucleoside on the silica gel followed by condensation with the added nucleoside through the 3'-OH. Alternatively, and preferably, the phosphite group is incorporated into the added nucleoside at the 3'-OH (the 5'-OH being blocked as by tritylating) and the resulting nucleoside phosphite then reacted with the 5'-OH of the nucleoside of the silica gel.

The deoxynucleoside-modified silica gel can also be condensed with a selected nucleoside through formation of a triester phosphite linkage between the 3'-OH of the deoxynucleoside of the silica gel and the 5'-OH of the selected deoxynucleoside. The phosphite linkage can be produced by first incorporating the phosphite group onto the 3'-OH of the nucleoside on the silica gel followed by condensation with the added nucleoside through the 5'-OH. Alternatively and preferably by this approach, the phosphite group is incorporated into the added nucleoside at the 5'-OH (3'-OH being blocked as by tritylating using art form procedures) and the resulting nucleoside phosphite then reacted with the 3'-OH of the nucleoside on the silica gel.

The general reaction can be represented by the following:

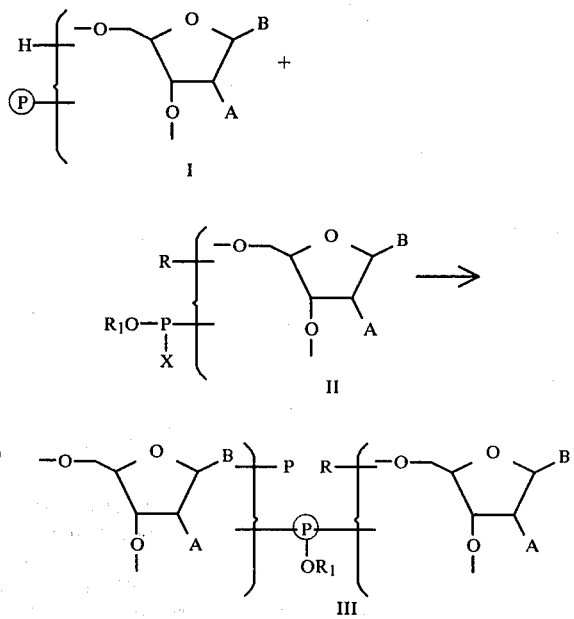

The preferred reaction is represented as follows:

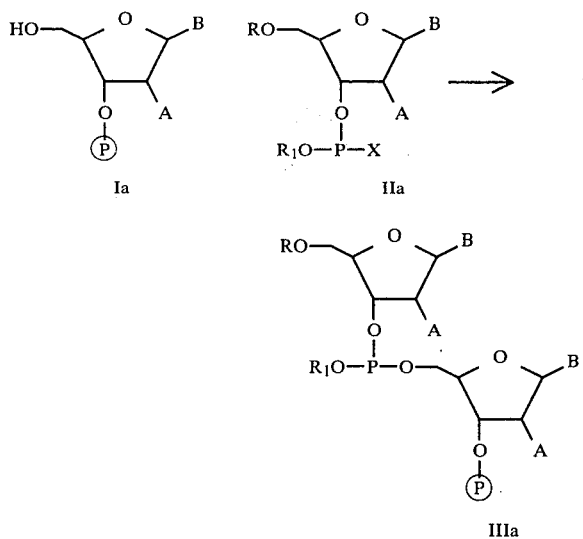

wherein ⓟ is an inorganic polymer linked to the 3' or 5'-O- of the nucleoside through a base hydrolyzable covalent bond; R is H or a blocking group; $R_1$ is a hydrocarbyl radical containing up to 10 carbons; each B is a nucleoside or deoxynucleoside base; and each A is H, OH or $OR_2$ in which $R_2$ is a blocking group; and X is halogen, preferably Cl or Br or a secondary amino group.

The compounds of structure II and IIa wherein X is a 2° amino group include those in which the amino group is an unsaturated nitrogen heterocycle such as tetrazole, indole, imidazole, benzimidazole and similar nitrogen heterocycles characterized by at least two ethylenic double bonds, normally conjugated, and which may also include other heteroatoms such as N, S or O. These compounds of structure II and IIa wherein X is such a heterocyclic amine, i.e., one in which the amino nitrogen is a ring heteroatom, are characterized by an extremely high reactivity, and consequently relatively low stability, particularly in the indicated preparation of compounds of structure III and IIIa. These phosphoramidites and the corresponding chloridites from which they are prepared are unstable to water (hydrolysis) and air (oxidation). As a consequence, such compounds can only be maintained under inert atmosphere, usually in sealed containers, at extremely low temperatures generally well below 0° C. Thus, the use of these compounds in the preparation of compounds of structure III and IIIa requires extreme precautions and careful handling due to the aforesaid high reactivity and low stability.

The present new compounds are of structure II and IIa wherein X is a certain type of secondary amino group. Specifically, the present new compounds are those in which X is a saturated secondary amino group, i.e. one in which no double bond is present in the secondary amino radical. More particularly, X is $NR_2R_3$, wherein $R_2$ and $R_3$ taken separately each represents alkyl, aralkyl, cycloalkyl and cycloalkylalkyl containing up to 10 carbon atoms, $R_2$ and $R_3$ when taken together form an alkylene chain containing up to 5 carbon atoms in the principal chain and a total of up to 10 carbon atoms with both terminal valence bonds of said chain being attached to the nitrogen atom to which $R_2$ and $R_3$ are attached; and $R_2$ and $R_3$ when taken together with the nitrogen atom to which they are attached form a saturated nitrogen heterocycle including at least one additional heteroatom from the group consisting of nitrogen, oxygen and sulfur.

The present new compounds are not as reactive as those of the aforesaid copending application and not as unstable. However, the present new compounds do react readily with unblocked 3'-OH or 5'-OH of nucleosides under normal conditions. The present new phosphoramidites are stable under normal laboratory conditions to hydrolysis and air oxidation, and are stored as dry, stable powders. Therefore, the present new phosphoramidites are more efficiently employed in the process of forming internucleotide bonds, particularly in automated processing for formation of oligonucleotides and polynucleotides as described in the aforesaid copending application.

Amines from which the group $NR_2R_3$ can be derived include a wide variety of saturated secondary amines such as dimethylamine, diethylamine, diisopropylamine, dibutylamine, methylpropylamine, methylhexylamine, methylcyclopropylamine, ethylcyclohexylamine, methylbenzylamine, methylcyclohexylmethylamine, butylcyclohexylamine, morpholine, thiomorpholine, pyrrolidine, piperidine, 2,6-dimethylpiperidine, piperazine and similar saturated monocyclic nitrogen heterocycles.

The nucleoside and deoxynucleoside bases represented by B in the above formulae are well-known and include purine derivatives, e.g. adenine, hypoxanthine and guanine, and pyrimidine derivatives, e.g. cytosine, uracil and thymine.

The blocking groups represented by R in the above formulae include trityl, methoxytrityl, dimethoxytrityl, dialkylphosphite, pivalyl, isobutyloxycarbonyl, t-butyl dimethylsilyl, and similar such blocking groups.

The hydrocarbyl radicals represented by $R_1$ include a wide variety including alkyl, alkenyl, aryl, aralkyl and cycloalkyl containing up to about 10 carbon atoms. Representative radicals are methyl, butyl, hexyl, phenethyl, benzyl, cyclohexyl, phenyl, naphthyl, allyl and cyclobutyl. Of these the preferred are lower alkyl, especially methyl and ethyl.

DESCRIPTION OF THE PREFERRED EMBODIMENTS

The preferred new compounds are those of structure IIa wherein X is di-lower alkyl amino, pyrrolidino, morpholino or piperidino, particularly preferred being the lower alkyl amino, especially dimethylamino and diethylamino; A is H; $R_1$ is lower alkyl; R is a trityl group; B is a nucleoside or deoxynucleotide base; and ⓟ is silica gel.

The new compounds of the present invention can be prepared according to art-recognized procedures such as by reaction of the selected secondary amine with the corresponding nucleoside phosphomonochloridite. This reaction is accomplished by dissolving the said nucleoside in an organic solvent, such as tetrahydrofuran or acetonitrile, and adding the selected secondary amine. After removing unwanted hydrochloride salt, the organic solvent solution of the phosphoramidite may be used as such for polynucleotide synthesis or the product can be isolated from the organic solvent solution and purified before further reaction.

As a further embodiment of the invention, the phosphoramidites are preferably prepared by forming the desired chloro-(2° amino)alkoxyphosphine and thereafter condensing this product with the selected nucleoside. This procedure obviates the difficulties of handling inherent in the case of the nucleoside phosphomonochlorodite which is susceptible to moisture hydrolysis and air degradation.

The reaction of the chloro-(2° amino)alkoxyphosphine is effected in an organic solvent solution of the selected nucleoside, preferably in the presence of a tertiary amine to take up the hydrogen chloride formed in the condensation reaction. The reaction proceeds smoothly at room temperature in a dry atmosphere and under an inert gas such as $N_2$ or helium. Organic solvents useful for this reaction include any solvent which will dissolve the reactants such as diethyl ether, chloroform, methylene chloride, ethylene chloride, ethyl acetate, and the like. The solution of product is separated from the precipitated hydrochloride salt of the added tertiary amine and can be used as such in forming polynucleotide or alternatively can be separated from the solvent and purified as by crystallization before further use. While the foregoing disclosure has mentioned the use of chloro compounds, it should be understood that bromo compounds can be used as desired with essentially the same results.

When the present new compounds are used in forming internucleotide bonds, they are preferably employed with proton donors. Thus, the phosphoramidites are activated by acidic compounds through protonation which facilitates the desired internucleotide bond formation. The acidic compounds to be employed for the purpose of the said activation are preferably mildly acidic and include, for example, amine hydrohalide salts and nitrogen heterocyclic compounds such as tetrazoles, imidazoles, nitroimidazoles, benzimidazoles and similar nitrogen heterocyclic proton donors. The amine hydrohalide salts to be used for the protonation activation are preferably tertiary amine salts, and, preferably, the hydrochloride salts, although hydrobromide, hydroiodide or hydrofluoride salts can also be used. The aforesaid tertiary amines include, for example, dimethylaniline, diisopropylaniline, methylethylaniline, methyldiphenylamine, pyridine and similar tertiary amines.

When the nucleoside is guanosine, i.e. where B is guanine, the use of amine hydrochlorides is not very effective for the purpose of activation, i.e. by protonation. With those compounds in which B is guanine, activation is preferably accomplished with the aforesaid nitrogen heterocyclic hydrogen donors.

Of course, as described in the aforesaid copending application, once the internucleotide bond is formed, the product is then further treated to remove blocking groups, e.g. blocking group R, which permits reaction with a further nucleoside of formula II herein and repeat reaction gives rise to the polynucleotide of determined sequence of nucleotides attached to the silica gel through the covalently-bonded linking groups, e.g. ester linking group.

After each nucleoside is added, the phosphite group preferably should be oxidized to phosphate, usually by reaction with iodine as oxidizing agent, although this can be accomplished by reaction with peroxides such as tertiary butyl peroxide and benzoyl peroxide, as well as hydroperoxides.

The oligonucleotide can then be obtained by hydrolytic cleavage to separate from the silica gel support, usually after removal of blocking groups such as R blocking groups and blocking groups on the nucleoside base moieties as described in the aforesaid copending application, generally by hydrolysis with ammonia.

As used herein the symbols for nucleotides and polynucleotides are according to the IUPAC-IUB Commission of Biochemical Nomenclature Recommendations [(1970) Biochemistry 9, 4022].

The following examples further illustrate the invention.

EXAMPLE I

Preparation of phosphoramidites of the formula:

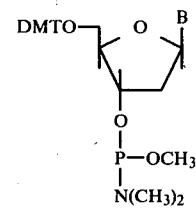

represented as compounds I–IV, in which in compound
I, B=1-Thyminyl;
II, B=1-(N-4-benzoylcytosinyl);
III, B=9-(N-6-benzoyladeninyl);
IV, B=9-(N-2-isobutyrylguaninyl);
and DMT=di-p-anisylphenylmethyl.

The synthesis of compounds I–IV begins with the preparation of chloro-N, N-dimethylaminomethoxyphosphine [$CH_3O$ P(Cl) N($CH_3$)$_2$] which is used a monofunctional phosphitylating agent. A 250 ml addition funnel was charged with 100 ml of precooled anhydrous ether ($-78°$ C.) and pre-cooled ($-78°$ C.) anhydrous dimethylamine (45.9 g, 1.02 mol). The addition funnel was wrapped with aluminum foil containing dry ice in order to avoid evaporation of dimethylamine. This solution was added dropwise at $-15°$ C. (ice-acetone bath) over 2 h to a mechanically stirred solution of methoxydichlorophosphine (47.7 ml, 67.32 g, 0.51 mol) in 300 ml of anhydrous ether. The addition funnel was removed and the 1 l., three-necked round bottom flask was stoppered with serum caps tightened with copper wire. The suspension was mechanically stirred for 2 h at room temperature, then filtered and the amine hydrochloride salt washed with 500 ml anhydrous ether. The combined filtrate and washings were distilled at atmospheric pressure and the residue under reduced pressure. The product was distilled at 40°–42° C. 13 mm Hg and was isolated in 71% yield (51.1 g, 0.36 mol). $d^{25}=1.115$ g/ml. $^{31}$P-N.M.R., $=-179.5$ ppm (CDCl$_3$) with respect to internal 5% v/v aqueous $H_3PO_4$ standard. $^1$H-N.M.R. doublet at 3.8 and 3.6 ppm $J_{P-H}=14$ Hz (3H, OCH$_3$) and two singlets at 2.8 and 2.6 ppm (6H, N(CH$_3$)$_2$). The mass spectrum showed a parent peak at m/e=141.

The 4'-O-di-p-anisylphenylmethyl nucleoside (1 mmol) was dissolved in 3 ml of dry, acid free chloroform and diisopropylethylamine (4 mmol) in a 10 ml reaction vessel preflushed with dry nitrogen. [CH$_3$OP(Cl)N(CH$_3$)$_2$] (2 mmol) was added dropwise (30–60 sec) by syringe to the solution under nitrogen at room temperature. After 15 min the solution was transferred with 35 ml of ethyl acetate into a 125 ml separatory funnel. The solution was extracted four times with an aqueous, saturated solution of NaCl (80 ml). The organic phase was dried over anhydrous Na$_2$SO$_4$ and evaporated to a foam under reduced pressure. The foam was dissolved with toluene (10 ml) (IV was dissolved with 10 ml of ethyl acetate) and the solution was added dropwise to 50 ml of cold hexanes (−78° C.) with vigorous stirring. The cold suspension was filtered and the white powder was washed with 75 ml of cold hexanes (−78° C.). The white powder was dried under reduced pressure and stored under nitrogen. Isolated yields of compounds I–IV were 90–94% (see Table I).

TABLE I

| COMPOUND | δ-$^{31}$P (ppm) (Acetone-d$_6$) | δ-$^{31}$P (ppm) (CDCl$_3$) | ISOLATED YIELD (%) |
|---|---|---|---|
| I | −146.0, −145.4 | −147.7, −146.8 | 93, 95* |
| II | −146.3, −145.5 | −148.0, −147.0 | 92, 95* |
| III | −146.1, −145.8 | −147.4, −147.3 | 90, 98* |
| IV | −145.9, −145.7 | −147.7, −147.2 | 90, 98* |
| Ia | −139.6, −138.9 | −140.8, −139.9 | 97** |
| IIa | −139.6, −139.0 | −140.6, −140.0 | 94** |
| IIIa | −139.7, −138.9 | −141.0, −139.9 | 97** |
| IVa | −140.3, −140.2 | −143.6, −141.9 | 93** |

*Estimated purity from $^{31}$P-N.M.R.
**Estimated yield from $^{31}$P-N.M.R.

The purity of the products was checked by $^{31}$P-N.M.R. Additionally, when analyzed by $^{31}$P-N.M.R., these compounds were stable for at least a month when stored at room temperature under nitrogen. Furthermore, no significant amount of (3′-3′)dinucleoside phosphite was detected by $^{31}$P-N.M.R. (less than 4%). The low content of the (3′-3′) dinucleoside phosphite represents a significant improvement over the prior art phosphite coupling procedure where a considerable amount of unwanted (3′-3′) dinucleoside phosphite was unavoidable.

The aminophosphoramidites I–IV were employed in condensation with 3′-O-blocked nucleosides to form internucleotide bonds. The phosphoramidites were activated by weak acids such as amine hydrochloride salts or tetrazoles.

A. In the following procedure, the process was monitored using $^{31}$P-N.M.R. In a 10 mm. N.M.R. tube, 1.2 molar equivalents of 3′-O-levulinylthymidine and collidine were added to a mixture formed by adding N,N-dimethylaniline hydrochloride (1 mmol) in 0.51 ml dry CDCl$_3$ at room temperature under N$_2$ to amidite compound I (0.5 mmol, −147.7 and −146.8 ppm) in 2 ml of dry, acid free CDCl$_3$ and an essentially quantitative yield of dinucleoside phosphite Ia (−140.8 and −139.9 ppm) was obtained.

B. Amidite compound I (0.5 mmol) and 3′-O-levulinylthymidine (0.6 mmol) were placed in a 10 mm N.M.R. tube and sublimed 1H-tetrazole (1.5 mmol) in 2.5 ml of dry acetonitrile-d$_3$ was added under nitrogen atmosphere. The $^{31}$P-N.M.R. spectrum was immediately recorded and displayed a quantitative yield of Ia. Similarly, dinucleosides were obtained when II, III and IV were reacted with 3′-levulinylthymidine as shown in Table I. The appropriate chemical shifts of compounds I–IV and Ia–IVa with respect to internal 5% v/v aqueous H$_3$PO$_4$ standard are reported in Table I.

EXAMPLE II

Alternate procedure for Chloro-N,N-disubstituted Aminomethoxyphosphine

A 50 ml dropping funnel was charged with 31.59 g of N,N-Dimethylaminotrimethylsilane (42.1 ml, 0.27 mol) which wad added dropwise over 1 h under nitrogen atmosphere to 25 ml of cold (−15° C.) methoxydichlorophosphine (35.15 g, 0.27 mol) in a 250 ml round bottom flask. A white unidentified precipitate formed during the course of the addition. Once the addition was finished, the ice-acetone bath was removed and the suspension was stirred at room temperature for 1 h. The reaction mixture was then slowly vacuum distilled through a one foot long, vacuum jacketed glass helices (3/32″) column. The product distilled at 40°–42° C. ¶ 13 mm Hg and was isolated in 81% yield (30.77 g, 0.22 mol). d$^{25}$ = 1.115 g/ml. $^{31}$P-N.M.R., = −179.5 ppm (CDCl$_3$) with respect to internal 5% aqueous H$_3$PO$_4$ standard. $^1$H-N.M.R. doublet at 3.8 and 3.6 ppm $^J$P-4 = 14 Hz (3H, OCH$_3$) and two singlets at 2.8 and 2.6 ppm (6H, N(CH$_3$)$_2$. The mass spectrum showed a parent peak at m/e = 141.

(Anal. calcd. for C$_3$H$_9$ClNOP: C, 24.45; H, 6.42; N, 9.90; O, 11.30; P, 21.88. Found C, 24.53; H, 6.20; N, 10.04; O, 11.08; P, 21.44.

The procedure was successfully applied to the preparation of chloro-N, N-diethylaminomethoxyphosphine and chloropyrrolidino-methoxyphosphine.

EXAMPLE III

The applicability of phosphoramidites I–IV to the synthesis of deoxyoligonucleotides on polymer supports was accomplished by condensing compounds I–IV with N-2-isobutyryldeoxyguanosine attached covalently to silica gel. Thus, N-2-isobutyryldeoxyguanosine (1 μmole) covalently attached to silica gel (20 mg) at the 3′-position, I (10 μmole), and 1H-tetrazole (50 μmole in 0.1 ml dry acetonitrile) were shaken for 20 min and the reaction was then quenched with aqueous lutidine. The same reaction sequence was effected with II, III and IV. After the usual oxidation and deprotection procedures, d(TpG), d(CpG), d(ApG) and d(GpG) were obtained in 100%, 98%, 94%, and 93% yield respectively (measured spectrometrically from the dimethoxytrityl cation using an extinction of 7 × 10$^4$ at 498 nm). These dinucleotides were completely degraded by snake venom phosphodiesterase and the appropriate nucleosides and ncleotides were obtained in the proper ratios (monitored via high pressure liquid chromatography analysis of snake venom phosphodiesterase hydrolysates).

The following deoxynucleotides have been synthesized using this procedure:

| | |
|---|---|
| d(C—T—C—A—A—A—T—G—G—G—T—C) | d(C—C—A—C—A—A—A—C—C—C) |
| d(A—A—A—T—G—C—G—A—C—C—C—A) | d(A—G—C—T—A—T—G—G—G—T—T—T) |
| d(T—T—G—A—G—C—C—A—A—C—A) | d(T—T—A—G—C—T—C—A—C—T—C—A) |
| d(T—C—A—T—C—C—T—G—T—T—G—G) | d(T—T—A—G—G—C—A—C—C—C) |
| d(G—G—G—C—C—G—A—A—T—T—G—T) | d(C—A—G—G—C—T—T—T—A—C—A) |
| d(C—G—G—C—C—C—C—T—T—A—C—T) | d(C—T—T—T—A—T—G—C—T—T—C) |
| d(T—C—C—T—C—A—A—G—T—A—A—G) | d(C—G—G—C—T—C—G—T—A) |
| d(T—G—A—G—G—A—T—A—A—A—T—T) | d(T—G—T—A—C—T—A—A—A—G) |
| d(A—T—G—T—G—T—G—A—T—T—T—A) | d(G—A—G—G—T—T—G—T—A—T—G) |
| d(G—T—G—G—T—A—A—A—T—C—A) | d(T—A—C—A—T—G—C—A—A) |

The detailed procedure utilized is as follows:

5'-O-DMT-N-benzoyldeoxyadenosine [DMT rd (bzA)] (0.66 g., 1 mmole) in dry THF (3 ml) is added dropwise under an argon atmosphere to a stirred solution of the THF (3 ml) containing methyldichlorophosphite (0.113 ml, 1.2 mmole) and 2, 4, 6 trimethylpyridine (0.633 ml. 4.8 mmole) at −78° C. After 10 minutes at −78° C., the reaction solution is filtered through a sintered glass funnel and solvent is removed by concentration in vacuo. Excess methyl phosphodichloridite is removed by dissolving the resulting gum in toluene: THF (2 ml, 2:1) and re-evaporating in vacuo to a gum. This procedure is repeated several times to insured removal of the dichloridite. The nucleoside phosphomonochloridite is converted to the tetrazolide. The gum resulting from the final re-evaporation is dissolved in THF (2 ml). A solution of the selected secondary amine 0.9 mmole) in THF (2 ml) is then added dropwise with stirring at −78° C. to the nucleoside phosphomonochloridite. After 10 minutes at −78° C., the solution is transferred to a centrifuge tube, spun at low speed, and the supernatant is removed. This solution contains the activated nucleoside phosphoramidite. If not used immediately, this phosphoramidite can be placed in long term storage after precipitation by dropwise addition into dry pentane, followed by collection, drying in vacuo, and storing in sealed tubes under argon or other inert gas at room temperature, or lower temperatures, e.g. 0° C. All operations are performed under inert gas to avoid oxidation. At no time is the active agent exposed to air.

The foregoing procedure is applicable for the preparation of activated thymidine, deoxycytidine, and deoxyadenosine nucleotides. For the preparation of the activated deoxyguanosine nucleotide, the procedure is the same except for the stoichiometry. The molar ratio of 5'-O-DMT-N-isobutyryldeoxyguanosine [DMTrd(ibG)]; methyldichlorophosphite; 2, 4, 6 trimethylpyridine and tetrazole is 1:0.9:3.8:0.7. The steps necessary for addition of one nucleotide to the modified silica gel polymer support follow. The removal of the dimethoxytrityl group from the nucleotide is accomplished by exposing the modified silica gel support to 0.1 M $ZnBr_2$ in nitromethane for 15 to 30 minutes. The support is then washed initially with butanol:2,6 lutidine:THF (4:1:5 by volume) and finally with THF. The solvent ratio is not important since this step is used to remove potential zinc esters of nucleosides. This step could be eliminated but lower yields may result. Other Lewis acids could be substituted for $ZnBr_2$, such as $BF_3$, $AlCl_3$ and $TiCl_4$. However $ZnBr_2$ is preferred. Protic acid can also be used. However approximately 3-5% depurination of each purine by protic acids is observed even when the amount of acid is reduced to the minimum amount needed to remove the dimethoxytrityl group. The next step in the process is condensation of the protected and activated nucleotide to the nucleoside or oligonucleotide covalently bound to the support. This is accomplished by using 10-15 equivalents of the activated phosphoramidite and a reaction time of about one hour. The solvent is anhydrous THF. The next step in the process is the blocking of unreacted 5'-hydroxyl groups. This is accomplished using a solution of acetic anhydride, dimethylaminopyridine, pyridine and THF. This may also be accomplished using a 0.33 M solution of diethylmonotriazolophosphite in 2,6-lutidine/THF (1:5 by volume). The reaction time is 5 min. and is followed by a THF wash. As a further alternative, a solution of phenylisocyanate/lutidine (45:55 by volume) and a 90 minute reaction time may be used for this step. This solution is then removed from the modified silica gel by washing the support with THF and with acetonitrile. The first procedure is preferred. This step can be eliminated or other reagents that react with 5'-hydroxyl groups and are compatible with the overall chemistry can be substituted therefore. However, by including this step, the final purification of the desirable oligonucleotide is rendered much easier. This is because the complexity of the total synthetic material bound to the support is reduced considerably. The final step in each cycle is oxidation of the phosphite to the phosphate. A composition of 0.1 M $I_2$ in water/2, 6 lutidine/THF (1:1:3) is preferred, although other ratios can be used. Furthermore, other oxidizing agents such as N-chlorosuccinimide or aryl or alkyl peroxides could also be used. T-butyl peroxide is presently preferred as oxidizing agent. After the addition of the appropriate activated nucleotides in any predetermined sequence, the deoxyoligonucleotide is removed from the support by base hydrolysis and blocking groups where present are also removed, either selectively i.e., stepwise, or in an overall hydrolysis treatment such as heating at 50° C. in ammonium hydroxide.

What is claimed is:

1. A compound represented by one of the formulae:

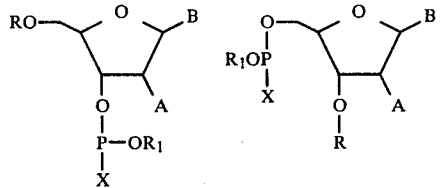

wherein B is a nucleoside or deoxynucleoside base; A is H, OH or $OR_2$ in which $R_2$ is a blocking group; R is a blocking group; $R_1$ is a hydrocarbyl radical containing up to about 10 carbon atoms; and X is $NR_2R_3$, wherein $R_2$ and $R_3$ taken separately each represent alkyl, aryl, aralkyl, cycloalkyl and cycloalkylalkyl containing up to 10 carbon atoms; $R_2$ and $R_3$ when taken together form an alkylene chain containing up to 5 carbon atoms in the principal chain and a total of up to 10 carbon atoms with both terminal valence bonds of said chain being attached to the nitrogen atom to which $R_2$ and $R_3$ are attached; and $R_2$ and $R_3$ when taken together with the nitrogen atom to which they are attached form a saturated nitrogen heterocycle including at least one additional heteroatom from the group consisting of nitrogen, oxygen and sulfur.

2. A compound represented by the formula:

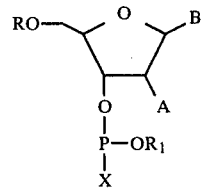

wherein B is a nucleoside or deoxynucleoside base; A is H, OH or $OR_2$ in which $R_2$ is a blocking group; R is a blocking group; $R_1$ is a hydrocarbyl radical containing up to about 10 carbon atoms; and X is $NR_2R_3$, wherein $R_2$ and $R_3$ taken separately each represent alkyl, aryl, aralkyl, cycloalkyl and cycloalkylalkyl containing up to 10 carbon atoms; $R_2$ and $R_3$ when taken together form an alkylene chain containing up to 5 carbon atoms in the principal chain and a total of up to 10 carbon atoms with both terminal valence bonds of said chain being attached to the nitrogen atom to which $R_2$ and $R_3$ are attached; and $R_2$ and $R_3$ when taken together with the nitrogen atom to which they are attached form a saturated nitrogen heterocycle including at least one additional heteroatom from the group consisting of nitrogen, oxygen and sulfur.

3. A compound according to claim 1 or 2 wherein R is a trityl group.

4. A compound according to claim 1 or 2 wherein R is a di-p-anisylphenylmethyl group.

5. A compound according to claim 1 or 2 wherein R is a p-anisyldiphenylmethyl group.

6. A compound according to claim 1 or 2 wherein $R_1$ is lower alkyl.

7. A compound according to claim 1 or 2 wherein x is di-lower alkylamino.

8. A compound according to claim 7 wherein X is dimethylamino.

9. A compound according to claim 1 or 2 wherein X is a saturated nitrogen heterocyclic.

10. A compound according to claim 9 wherein the nitrogen heterocyclic is piperidine, morpholine, or piperazine.

11. A compound according to claim 1 or 2 wherein B is adenine, guanine, cytosine, uracil and thymine.

12. The compound according to claim 2 wherein R is di-p-anisylphenylmethyl, B is 9-(N-6-benzoyladeninyl), $R_1$ is methyl, A is H and X is dimethylamino.

13. The compound according to claim 2 wherein R is di-p-anisylphenylmethyl, B is thyminyl, $R_1$ is methyl, A is H and X is dimethylamino.

14. The compound according to claim 2 wherein R is di-p-anisylphenylmethyl, B is 1-(N-4-benzoylcytosinyl), $R_1$ is methyl, A is H and X is dimethylamino.

15. The compound according to claim 2 wherein R is di-p-anisylphenylmethyl, B is 9-(N-6-benzoyladeninyl), $R_1$ is methyl, A is H and X is piperidino.

16. The compound according to claim 2 wherein R is di-p-anisylphenylmethyl, B is 9-(N-2-isobutyrylguaninyl), $R_1$ is methyl, A is H and X is dimethylamino.

17. A compound according to claim 1 wherein X is selected from the class consisting of dimethylamino, diethylamino, diisopropylamino, dibutylamino, methylpropylamino, methylhexylamino, methylcyclopropylamino, ethylcyclohexylamino, methylbenzylamino, methylcyclohexylmethylamino, butylcyclohexylamino, morpholino, thiomorpholino, pyrrolidino, piperidino, 2,6-dimethylpiperidino and piperazino.

18. A compound according to claim 1 wherein X is diisopropylamino.

19. A compound according to claim 2 wherein X is selected from the class consisting of dimethylamino, diethylamino, diisopropylamino, dibutylamino, methylpropylamino, methylhexylamino, methylcyclopropylamino, ethylcyclohexylamino, methylbenzylamino, methylcyclohexylmethylamino, butylcyclohexylamino, morpholino, thiomorpholino, pyrrolidino, piperidino, 2,6-dimethylpiperidino and piperazino.

20. A compound according to claim 2 wherein X is diisopropylamino.

* * * * *